(12) United States Patent  
Lian et al.

(10) Patent No.: US 9,383,256 B2
(45) Date of Patent: Jul. 5, 2016

(54) UV DOSIMETRY SYSTEM WITH SENSOR DATA CORRECTION

(71) Applicants: Jie Lian, Beaverton, OR (US); Nabyl Bennouri, Tualatin, OR (US); Nattapon Chaimanonart, Lake Oswego, OR (US)

(72) Inventors: Jie Lian, Beaverton, OR (US); Nabyl Bennouri, Tualatin, OR (US); Nattapon Chaimanonart, Lake Oswego, OR (US)

( * ) Notice: Subject to any disclaimer, the term of this patent is extended or adjusted under 35 U.S.C. 154(b) by 0 days.

(21) Appl. No.: 14/575,983

(22) Filed: Dec. 18, 2014

(65) Prior Publication Data

US 2015/0177063 A1  Jun. 25, 2015

Related U.S. Application Data

(60) Provisional application No. 61/918,153, filed on Dec. 19, 2013.

(51) Int. Cl.
| | |
|---|---|
| *G01J 1/42* | (2006.01) |
| *G01T 1/02* | (2006.01) |
| *G06F 1/16* | (2006.01) |
| *G01J 1/02* | (2006.01) |
| *G01J 1/04* | (2006.01) |
| *A61B 5/00* | (2006.01) |
| *G01J 1/44* | (2006.01) |

(52) U.S. Cl.
CPC .............. *G01J 1/429* (2013.01); *A61B 5/441* (2013.01); *G01J 1/0219* (2013.01); *G01J 1/0233* (2013.01); *G01J 1/0403* (2013.01); *G01J 1/44* (2013.01); *G01T 1/02* (2013.01); *G06F 1/163* (2013.01); *G01J 2001/4266* (2013.01); *G01J 2001/444* (2013.01)

(58) Field of Classification Search
CPC ........... G01J 1/44; G01J 1/429; G01J 1/0403; G01J 2001/444
USPC ........................................................ 250/372
See application file for complete search history.

(56) References Cited

U.S. PATENT DOCUMENTS

| | | | |
|---|---|---|---|
| 6,735,550 B1 * | 5/2004 | Weekley et al. ............... | 702/182 |
| 2007/0237354 A1 * | 10/2007 | Zhou ............................. | 382/100 |
| 2012/0326046 A1 | 12/2012 | Aslam et al. | |
| 2015/0041663 A1 * | 2/2015 | Oliver et al. .................. | 250/372 |

OTHER PUBLICATIONS

Godar DE, Pope SJ, Grant WB, Holick MF. Solar UV doses of young Americans and vitamin D3 production. Environ Health Perspect Jan. 2012;120:139-143.

(Continued)

*Primary Examiner* — David Porta
*Assistant Examiner* — Abra Fein

(57) ABSTRACT

A UV exposure dosimetry system includes at least one UV sensor that accurately measures the UV irradiance intensity. The system can generate extrapolated UV intensity data based on measured UV intensity data to correct unreliable UV measurement due to inconsistent irradiation of UV light. The UV dosimetry system integrates the extrapolated UV intensity data over time to calculate the real-time UV dosage and the vitamin D production by taking into account factors comprising UV sensor location, body surface area, clothing coverage, and sunscreen usage. Based on the measurement, the system can predict the time remaining to skin burn and the time remaining to reach daily goal of vitamin D production. The UV dosimetry system supports multi-user control through an advanced and user friendly input and output interface.

20 Claims, 7 Drawing Sheets

(56) References Cited

OTHER PUBLICATIONS

Pope SJ, Godar DE. Solar UV geometric conversion factors: horizontal plane to cylinder model. Photochem Photobiol Mar.-Apr. 2010;86:457-466.

Thieden E, Agren MS, Wulf HC. The wrist is a reliable body site for personal dosimetry of ultraviolet radiation. Photodermatol Photoimmunol Photomed. Apr. 2000;16(2):57-61.

* cited by examiner

UV DOSIMETRY SYSTEM WITH SENSOR DATA CORRECTION

CLAIM OF PRIORITY

This application claims the benefit of priority under 35 U.S.C. §119(e) of U.S. Provisional Application No. 61/918,153, entitled "UV DOSIMETRY SYSTEM", filed on Dec. 19, 2013, which is hereby incorporated by reference.

1. FIELD OF THE INVENTION

The present invention relates generally to a system and methods for measuring the ultraviolet (UV) irradiation dosage and usage of such information for calculating the vitamin D production, for analyzing and displaying related UV information, and for guiding users to achieve optimal UV exposure.

2. BACKGROUND

Optimal Balance of Sun Exposure

UV exposure is known to have both detrimental and beneficial effect. Over exposure to sunlight can cause sunburn, skin aging, and skin cancer, whereas insufficient sunlight exposure can lead to vitamin D deficiency, which is associated with many health maladies. Therefore, there has been a growing consensus among many public health organizations that there needs to be a balance between the risks of having too much and the risks of having too little sunlight. However, the goal of achieving optimal balance of UV exposure remains elusive, since there is no definition of what is considered to be the optimal UV dosage, and consequently there is no quantitative means to assess whether a person's UV exposure is optimal or suboptimal. Therefore, there is a need to provide a system and method for quantitative evaluation the optimal balance of UV exposure, by taking into account both skin damage and vitamin D production effects of UV light. However, to develop a solution for this problem, there are several additional challenges that need to be overcome, as described below.

Safe Sun Exposure Time

One of the challenges is to quantify the damaging effect of UV exposure, which can be immediate and long-term. Sunburn is noticeable 3-4 hours after over exposure of UV light, peaking at around 24 hours. The long-term effects of excessive UV exposure include photo-aging, immunosuppression, and carcinogenicity. Since sunburn is a frequent detrimental effect on human skin, the CIE erythemal action spectrum is often recommended for use in assessing the skin damaging effect of UV radiation. The minimal erythemal dose (MED) is used to describe the erythemal potential of UV radiation, and 1 MED is defined as the effective UV dose that causes a perceptible reddening of previously unexposed human skin. The MED is known to vary between individuals, and is affected by many factors such as the skin type. Therefore, personalized UV irradiance dose monitoring is important. For a UV monitoring system, it is important to predict how long a person can safely stay exposed to sunlight before getting sunburn. The time to skin burn is a dynamic parameter. It is affected by the time varying intensity of UV irradiance. It also depends on the accumulated UV dose already received by the person. Moreover, it can be modified by the person's behaviors, such as seeking the shade, changing clothing coverage, applying the sunscreen, etc. To the best knowledge of the inventors, there is no existing solution for dynamic estimation of a person's safe sun exposure time.

Cutaneous Vitamin D Synthesis

Another challenge is to quantify the UV induced cutaneous vitamin D synthesis. Vitamin D, commonly known as the sunshine vitamin, actually functions as a hormone. Its main biologic function in people is to maintain serum calcium and phosphorus concentration within the normal range. Sufficient vitamin D is not only important for bone health, but also may decrease the incidence of diabetes, inhibit some autoimmune diseases such as multiple sclerosis, reduce the mortality from common cancers and cardiovascular diseases, among many other health benefits. However, studies have shown that many people do not go outside enough to meet their minimum vitamin D needs. In fact, vitamin D deficiency is now recognized as a pandemic. Therefore, there is a need for a solution to calculate daily vitamin D production resulting from UV exposure, and to provide user useful information to determine if vitamin D supplement is necessary, and if so, how much is necessary.

Effective Sun Protection Factor

A person's UV exposure is affected by the usage of sunscreen. The sun protection factor (SPF) is widely used to measure the effectiveness of a sunscreen in affording photoprotection to subjects exposed to sources of UV radiation that may produce cutaneous erythema. According to the U.S. Food and Drug Administration and international protocols, SPF shall be determined by using a prescribed sunscreen application thickness of 2.0 mg/cm$^2$. However, many studies have shown that users typically apply much less sunscreen during leisure time than the suggested 2.0 mg/cm$^2$, typically between 0.5 and 1.5 mg/cm$^2$. Moreover, after a sunscreen is applied to the skin, it is commonly removed to a greater or lesser extend because of activities such as swimming, toweling, or excessive sweating and rubbing. Thus, frequent and regular reapplication of sunscreen is often recommended for users who experience extended period of sun exposure, but the optimal frequency and amount of sunscreen reapplication remain inconclusive. For these reasons, the effective SPF of a sunscreen product often actually deviates from the labeled SPF. Therefore, a solution is needed for dynamic calculation the effective SPF of the applied sunscreen. This is important for at least two reasons. First, it allows more accurate estimation of the accumulated UV dose received by the subject, thus can help user to better protect against skin damage caused by over exposure of UV radiance. Second, since a high SPF sunscreen dramatically reduces the skin's capability to synthesize vitamin D, knowing the effective SPF allows more accurate estimation of the vitamin D production.

Exposed Body Surface Area

Because only skin surface exposed to sunlight can synthesize vitamin D, different clothing choices can significantly affect the amount of vitamin D production in a person. Therefore, to estimate the amount of cutaneous vitamin D synthesis based on the UV dosage, it is important to know the percentage of exposed body surface area, taking into account of various options of clothing coverage. Consequently, there is a need for a solution to efficiently calculate the exposed body surface area corresponding to common clothing choices in order to accurately measure a user's vitamin D production.

Reliable UV Sensor Measurement

Yet another challenge is to reject or correct unreliable UV sensor measurement. If the UV sensor is not aligned with the direct solar irradiance, the sensor measurement may underestimate the UV intensity at surfaces that are normal to the sunlight. In particular, the angle sensitivity of UV sensor with respect to sunlight poses a practical challenge for a wearable UV dosimeter, since its orientation can change anytime as the user varies position and/or posture while the sun irradiance angle also varies constantly. Even subtle change of sensor orientation and/or the shade coverage caused by user movement can dramatically change the sensor measurement. Thus the direct measurement from the wearable UV dosimeter may be less than the actual UV intensity on the user's body surface that is normal to the sun light. Therefore, in order to more accurately estimate the UV dosage received by the user, there is a need for a solution to filter out the unreliable UV sensor measurement.

Sun Exposure Time

Solar radiation has been used since ancient times to treat various diseases. Although the beneficial effects of solar radiation are mainly mediated via UV induced vitamin D production in skin, several other pathways may exist for the action of UV radiation on humans. In particular, exposure to sunlight has mood enhancing effect, which is believed to be mediated through the release of serotonin. Research has shown that the rate of production of serotonin by the brain was directly related to the prevailing duration of bright sunlight, and rose rapidly with increased luminosity. The concept—that sunlight has beneficial effects on the serotonin system and the mood and stability of humans—is consistent with the idea that serotonin is involved in homeostasis in humans and contributes to the emergence of mind. Therefore, there is a need for a solution to calculate the daily sun exposure time (SET), thus allowing user to potentially correlate SET with her/his mood of the day. Such a feature may not only reveal the likely correlation between mood and SET, but also provides the user guidance to enhance mood by consciously adjusting SET.

Prediction of Optimal Sun Exposure Time

While it is helpful for a person to obtain instant feedback on received UV dose and cutaneous vitamin D production and use such information as a guidance to optimize sun exposure, more benefits can be gained if the person knows in advance how to spend time outdoors in the near future for optimal sun experience. For example, it would be very helpful if a person knows what time and how long to stay outside in the next few days to avoid sun damage and to generate sufficient vitamin D. Therefore, there is a need for a solution to provide the user predictive information on optimal sun exposure in the near future, so that the user can plan ahead based on such information.

3. SUMMARY OF THE INVENTION

The challenges described above are solved by the present invention as described below.

It is an objective of this invention to provide a system and method for monitoring a person's UV exposure, and using such information to provide feedback and guidance to the user for achieving optimal balance between the risk and benefits of UV exposure.

It is another objective of this invention to provide a system and method for dynamic estimation of a person's safe sun exposure time.

It is a further objective of this invention to provide a system and method for calculating a person's vitamin D production resulting from UV exposure.

It is yet a further objective of this invention to provide a system and method for dynamic calculating the effective SPF of the applied sunscreen.

Another objective of this invention is to provide a system and method for calculating a person's exposed body surface area corresponding to common clothing choices.

Yet a further objective of this invention is to provide a system and method for calculating a person's the daily sun exposure time.

Yet it is also an objective of this invention to provide a system and method for providing predictive information to the user to guide optimal sun exposure in the near future.

According to this invention, a personal UV dosimetry system comprises a wearable unit and a mobile computing device. The wearable unit comprises a circuitry for measuring the irradiating UV intensity, and the wearable unit is capable of wirelessly communicating with the mobile computing device. The mobile computing device has the software application that can display, store, edit, analyze, and provide summary report of the data collected by the wearable unit, and may further communicate with a remote server, which can save the measured data in a secure database, and such data becomes accessible from other mobile devices or directly from a webpage protected by a password.

By analyzing the measured UV intensity data, the UV dosimetry system not only can calculate the real-time UV index (UVI), but also UV dose actually received by the subject and vitamin D production within a time period, taking into account of various factors such as the skin type, the sunscreen usage, the sensor location, etc.

By analyzing data about UV dose and vitamin D production, the UV dosimetry system calculates a new metric that can quantitatively evaluate the optimal balance of UV exposure, by taking into account of both skin damage and vitamin D production effects of UV light. The new metric is preferably calculated and displayed in real-time by a wearable UV dosimeter that provides a visual feedback and guidance to the user for achieving optimal balance between the risk and benefits of UV exposure. The UV dosimetry system has a number of unique features, including real-time estimation of the safe sun exposure time, and calculation of cutaneous vitamin D production due to UV exposure. The UV dosimetry system implements advanced algorithms to improve the accuracy of calculation by taking into account of dynamic behavior of SPF, exposed body surface area, and signal processing of UV intensity data to reject or correct unreliable measurement. The UV dosimetry system also calculates the daily sun exposure time (SET), thus allowing user to potentially correlate SET with her/his mood of the day. Moreover, the UV dosimetry system can be individually customized by taking into account various factors, such as the subject's skin type, age, body surface area, and clothing coverage, the usage of sunscreen, the location of the wearable unit, etc. In addition, the UV dosimetry system can provide predictive information based on available forecast data to advise user what time and how long to stay outside in the next few days to avoid sun damage and to generate sufficient vitamin D.

The unique advantages of the present invention will be appreciated by people of ordinary skill in the art after referring to the written description of the invention in conjunction with the illustrative drawings.

4. BRIEF DESCRIPTION OF THE DRAWINGS

5. DETAILED DESCRIPTION

General Description of the System Components

Figure 1:
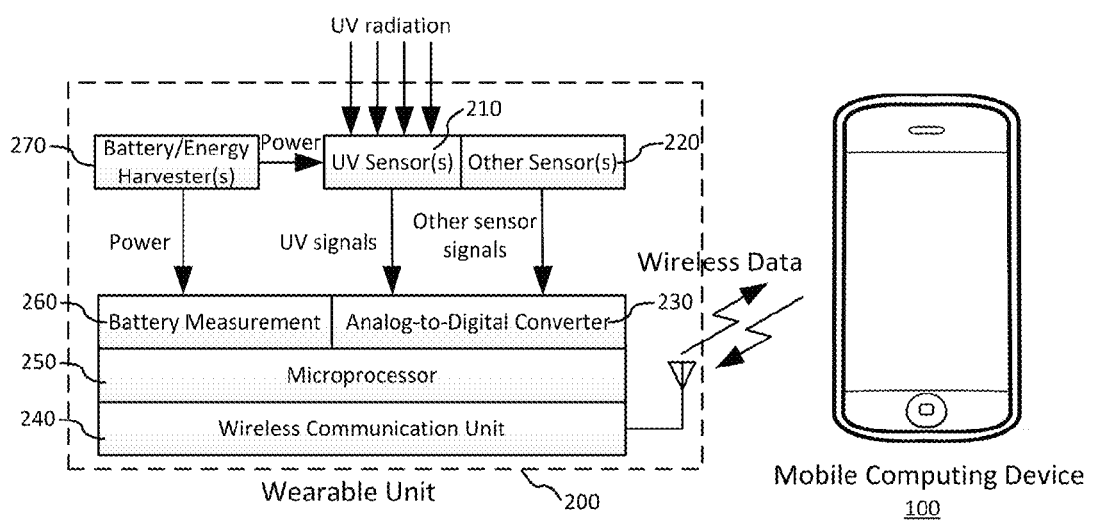
FIG. 1 shows the high level block diagram of the UV dosimeter system comprising a wearable unit and a mobile computing device.

According to a typical embodiment of this invention, the personal UV dosimetry system comprises a UV sensing unit and a mobile computing unit. The UV sensing unit comprises a circuitry for measuring the irradiating UV intensity. The UV sensing unit is capable of wirelessly and bi-directionally communicating with the mobile computing unit, such as a smart phone or a tablet computer. As known in the art, the mobile computing unit usually has rechargeable battery, a built-in camera, a location/navigation system such as the Global Positioning System (GPS), a user interface for receiving user input and generating various types of output, including but are not limited to, high resolution display, user notifications (e.g. via sound, vibration, text message, etc). The mobile computing unit runs an operating system (e.g. iOS, Android, etc.) and is capable of wireless connection to a communication network. The mobile computing unit has the software application that can display, store, edit, analyze, and provide summary report of the data collected by the UV sensing unit. The UV measurement data collected by the UV sensing unit and analyzed by the mobile computing unit includes not only UVI, but also UV dose actually received by the subject and vitamin D production within a time period, taking into account of various factors such as skin type, sunscreen usage, etc. In addition, the mobile computing unit can simultaneously tracks multiple users and/or multiple UV sensing units. Yet according to another embodiment of this invention, the UV dosimetry system is an integrated device that comprises both the UV sensing unit and the mobile computing unit. In other words, all the functions of the mobile computing unit described above are physically integrated together with the UV sensing unit, thus eliminating the need of two separate units and the wireless communication between them. For the purpose of illustration, we describe in the following the UV dosimetry system comprising two separate units (i.e. the UV sensing unit and the mobile computing device) as an example, while it should be understood that the same concept also applies to the UV dosimetry system with integrated UV sensing unit and the mobile computing unit.

According to one embodiment of this invention, the UV sensing unit is a wearable unit, which is a stand-alone, miniature device with aesthetic design, and is preferably waterproof. The wearable unit has a plurality of connecting mechanisms (e.g. clip, button, adhesive surface, etc.) that enable it to be easily adapted to be worn by an individual at various body parts. For example, the wearable unit can be worn as a clothing button, or a necklace, or wrist band, or hat accessory, etc.

According to another embodiment of this invention, the UV sensing unit is integrated with another article of manufacture. For example, the UV sensing unit can be a built-in unit of a cooler, a beach chair, an umbrella, a pair of eye classes or goggles, a headband, a roof-top weather station, etc. In another example, the UV sensing unit can be woven into the clothing such as shirts, jackets, scarf, etc., to be part of the so-called smart clothing. By embedding the UV sensing unit in textiles, the UV dosimetry system can become truly wearable.

In the following, we describe the UV dosimetry system by referring a wearable unit as an example of the UV sensing unit, although it should be understood that the UV sensing unit can take different forms as disclosed above.

FIG. 1 shows the high level block diagram of the UV dosimeter system comprising a wearable unit 200 and a mobile computing device 100. The UV radiation can be detected by one or more built-in UV sensors 210, which transform incident radiant UV signals into standard electrical signals. Semiconductor UV sensors fabricated using Silicon, Silicon-Carbide, Gallium-Nitride, Gallium-Arsenide and Germanium may be used as UV sensors due to their wide band-gap properties. The UV signals corresponding to the UV radiation intensity may be further digitized by an analog-to-digital converter 230. Other sensors 220 such as temperature sensors and humidity sensors can be included into the unit for enhanced system features. All detected sensing signals are processed by a microprocessor 250, and the acquired sensor data can be temporarily stored in a local memory circuit. The arranged data is then wirelessly sent to the mobile computing device for post data processing. A wireless communication unit 240 employing a wireless technology standard such as Bluetooth technology can be used to wirelessly transmit and receive data between the wearable unit 200 and the mobile computing device 100. Battery cells 270 such as a battery button cell can be used to power the wearable unit 200. Energy harvesters such as thermal electric generator or solar cell can be used as an alternative source of energy to power the wearable unit. The battery measurement block 260 may be included for enhanced features including monitoring the battery usage and determining device false operating conditions.

General Description of the System Operation

Figure 2:
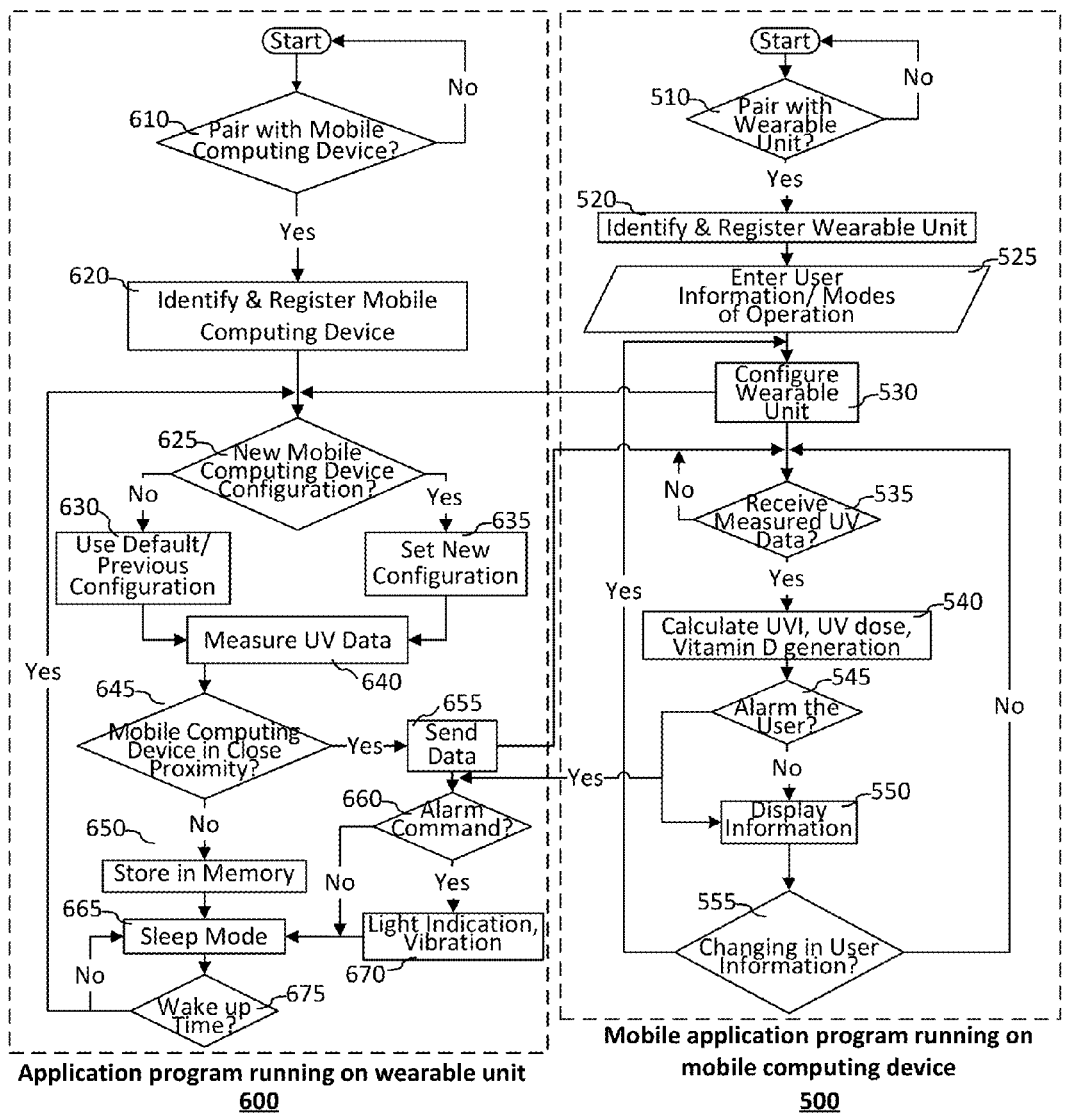
FIG. 2 shows the high level operation flowchart of the application software program running on the wearable unit and the application software program running on the mobile computing device, and the communication between thereof.

As shown in FIG. 2, the application program 600 running on the wearable unit controls the operation of the wearable unit 200. After the wearable unit 200 is turned on, the application program 600 starts advertising the data 610 through the wireless communication protocol 610 to pair with the mobile computing unit 100. The mobile application program 500 running on the mobile computing device 100 then tries to discover the advertising data pocket 510 to pair with the wearable unit 200. Once the broadcasting data is detected, an authentication process begins where both wearable unit 200 and mobile computing device 100 exchange the data to establish a connection. Several connection processes may be attempted until the connection is established, and the pair of wearable unit 200 and the mobile computing unit 100 identify and register with each other (620, 520) by respective application programs. The mobile application program 500 can notify users for a status of this pairing process. The mobile application program 500 can keep a record of the previous registered wearable units 200, thus the pairing process can be expedited in the future. Through the mobile application program 500, the user can edit modes of operation as well as personal information 525 such as the skin type, age, wearable position, and sun protection factor (SPF), etc. Some user information can be detected by employing a mobile computing peripheral unit. For example, the skin type may be detected by analyzing an image captured by a mobile computing camera. SPF lotion data can be detected by scanning the barcode on a lotion bottle. Based on received UV data 535 measured and sent from the wearable unit 200 and the entered user information 525, the mobile application program 500 can calculate the UVI, UV dose, and the amount of vitamin D production 540. Users can change the personal information 555 such as sunscreen usage and clothing coverage at any time so that the updated user information can be used for calculating UV dose and vitamin D production. User can also check the UV dose and related information such as vitamin D production through the mobile application program 500 anytime. The application program features will be described later in this disclosure. The wireless data communication between the wearable unit 200 and the mobile computing device 100 is automatically running in the background to make the mobile application program 500 user friendly and easy to use.

General Description of the Communication Protocol

Both mobile computing device 100 and wearable unit 200 are linked together through a communication protocol as demonstrated in the high level flowchart shown in FIG. 2. After the pairing connection process is established, the user programmable modes of operation 525 corresponding to commands and configurations for the wearable unit 200 such as the UV sample time, number of the UV data samples and UV data resolution are wirelessly transmitted 530 to the wearable unit 200 to determine if configuration update is necessary 625. Based on the received commands 625, the wearable unit 200 will either keep previous configurations 630 or set new configurations 635 for measuring UV data 640. These configurations determine how the UV data is measured and how often the data is wirelessly transmitted to the mobile computing device 100. For example, if a user wants to know the current UVI irradiating on the wearable unit 200, the data can be immediately sampled and transmitted to the mobile computing device 100. If the mobile computing device 100 is not in close proximity of the user 645, the sampled UV data can be temporarily stored in the local memory 650 of the wearable unit 200 for later transmission whenever the mobile computing device 100 is within the range to establish a pairing connection. In order to save the wearable unit battery consumption, all or parts of the electronic circuitries especially the wireless communication circuit could be powered down into a sleep mode 665, which consumes a minimal power. The wearable unit 200 goes into sleep mode whenever there is no active data sampling/processing or communication with the mobile computing device 100, and typically wakes up automatically 675 according to configured sampling period and communication protocol. A limited data processing and calculation on the wearable unit 200 can be implemented to reduce a firmware complexity on the microprocessor 250 and minimize the wake-up time for power saving. Therefore, most of the post data processing such as calculation of UV dose and vitamin D generation can be performed in the mobile computing device 100 as illustrated in FIG. 2. The results of the calculation can be sent back to the wearable unit 200 through wireless communication. Alternatively, if the mobile computing device 100 is out of the communication range of the wearable unit 200, the data processing and calculation could be performed by the microprocessor 250 on the wearable unit 200. If the calculated data results in a necessary user alert 545, the alarm mechanism is activated. The alarm mechanism could be an alarm sound, flashing screen/light or vibration generated by the mobile computing device 100, or the wearable unit 200, or both. For example, the alarm can be generated by the mobile computing device 100 to display related alarm information 550. Meanwhile, an alarm command 660 can be sent to the wearable unit 200 which also generates a user perceptible light and/or vibration alert 670.

As shown in FIG. 2, communication between the wearable unit 200 and the mobile computing device 100 is periodic for maintaining connection. The polling mechanism where one device broadcasts data and waits for another device acknowledges is used for notifying the connection status. If the time between broadcasting and waiting for acknowledgment is beyond a programmable communication time-out, connection is lost. With several failing reconnection attempts, the sampled UV data is then stored in the local memory circuit 650. Whenever the mobile computing device 100 is within the range 645 to establish a successful connection, the previously stored data is automatically transmitted 655 to the mobile computing device 100. By evaluating the received signal strength sent by the wearable unit 200, the mobile device 100 can implement the electronic leash function to estimate the distance to the wearable unit 200 and determine if it is within or outside the communication range.

Since the wearable unit 200 and the mobile computing device 100 are coupled together via wireless communication, the periodic status updates such as electronic leash notification, battery indication and memory indication can be wirelessly transmitted along with the measured UV data. Alarm can be generated by the wearable unit 200, or the mobile computing device 100, or both to alert the user of abnormal system conditions (e.g. memory full, low battery, communication lost, etc.). Therefore, it allows the UV dosimetry system operate without any interruptions due to electronic unleash, low battery or lack of memory. As a result, the accuracy and reliability of the system increases.

General Description of the User Interface

The wearable unit is by default in a sleep mode and the user can activate the measurement of the UVI, UV dose, and vitamin D production. The mobile device app can start, pause, resume, stop, and reset the measurement. The wearable unit can also start, pause, resume, and reset the measurements with user input, such as finger taps on a touch sensing area. For example, different numbers and/or sequences of taps can mean different commands.

The mobile device and the wearable unit can trigger sound, light, or vibration alarms when the accumulated UV dose is close to the harmful level. The wearable unit can also indicate the status or measurement results such as UVI, for example, with a few LEDs laid out in a circle or line. The mobile device can instantly query the measurements from the wearable unit. It can also display, store, edit, analyze, and provide summary report of the data collected by the wearable unit.

The mobile application syncs with a remote server to save the sensor measurement data in a secure database. This data becomes accessible from other mobile devices or directly from a webpage protected by a password. Using a software application, the data can be analyzed and presented in easy to understand graphs, tables, and summary reports. The user can share the data through social media, email, or text message.

Annotations can be added to the data for tagging purposes. For example, through annotation, the user can then remember when the data has been taken. The user can also annotate relevant events such as applying a sunscreen lotion, changing clothes, staying indoors, taking vitamin D supplement, etc.

The UV dosimetry system can accurately measure the location specific UVI in real time, which is more precise than the UVI forecast predicted by weather services. The UVI measurement by a user wearing the wearable unit can be posted in crowd sourcing websites or on a dedicated server and shared in the mobile device app so that anybody can access it. Since the UVI measurement could be misleading, e.g. if the user is in the shade, the app takes into account the forecasted UVI and/or the temperature of the device to decide if the measurement is valid or not. If it is valid then it is pushed to the servers. Otherwise it is discarded.

The mobile device also provides a user interface that allows user to change profile settings (e.g. age, gender, height, weight, etc.) and/or programming parameters. For example, user can select options and/or parameters that affect the calculation of UV dose and vitamin D production, such as clothing coverage, sunscreen type, etc.

Method for Multi-User Management

Multiple users can take advantage of one single wearable unit. The mobile application can create several accounts protected by a password. Each account saves its own data associated with one individual user. In addition, each account can create several profiles for the associated user. A profile is a configuration for a specific measurement of UV dose and/or vitamin D production. For example, it can include the clothes type worn and the sunscreen SPF used. Profiles are used to avoid setting the same parameters multiple times.

The mobile application can also track several wearable units at the same time. Each wearable unit can trigger a different alarm and an electronic leash allows the app to detect when a wearable unit is out of range by setting a sound, vibration, or light alarm on the mobile device and/or the wearable unit. Multi-user tracking is convenient, for example, for a parent or a caregiver to monitor UV exposure of several children. In addition, by utilizing the electronic leash function, the mobile device can operate in a search mode that allows the mobile app to find a lost wearable unit.

Optimal Balance of UV Exposure

This invention provides a novel solution for monitoring a person's UV exposure, and using such information to provide feedback and guidance to the user to optimize his/her sun experience. Specifically, in this section, we describe a method which can be implemented in the UV dosimetry system to quantitatively evaluate the optimal balance of UV exposure, by taking into account of both skin damage and vitamin D production effects of UV light. The described new metrics can be calculated and displayed in real-time by a UV dosimetry system that provides a visual feedback and guidance to the user for achieving optimal balance between the risk and benefits of UV exposure.

One new metric is termed UV exposure score (UVES), which is a normalized index ranging from 0 to 1 (or 0-100 by applying a scale factor 100). Higher UVES indicates improved UV balance whereas lower UVES indicates less optimal UV balance (obviously, it is equivalent to define UVES in the complementary form 1-UVES, so that lower value indicates improved UV balance whereas higher value indicates less optimal UV balance). For example, the UVES can be defined as:

$$\text{UVES} = \text{pvd}^V \cdot (1 - \text{puv}^U) \quad (1)$$

where pvd is the percentage of vitamin D production toward the daily goal, puv is the percentage of accumulated UV dose against the limit of safe UV dose, and V and U are two positive parameters that can be predefined or programmed by the user.

Clearly, UVES is the product of two terms, $\text{pvd}^V$ and $1-\text{puv}^U$, which respectively quantify the benefit of UV (e.g. vitamin D production) and residual risk of UV damage (e.g. sunburn). The weight of these two terms can be adjusted by parameters V and U, which can be predefined or programmed by the user of the UV dosimetry system.

The method of calculating vitamin D production is described below in the section titled "Calculation of Cutaneous Vitamin D Synthesis." The daily goal of vitamin D production (in unit of IU) is defined by the user, and $\text{pvd}^V$ is limited to the upper ceiling 1.0 (i.e. $\text{pvd}^V$ is fixed to 1 when the synthesis of vitamin D exceeds the daily goal). The method of calculating the accumulated UV dose is described below in the section titled "Calculation of Safe Sun Exposure Time." The limit of safe UV dose is defined by the user, typically being set to the user-specific minimal erythemal dose (MED). Similarly, $\text{puv}^U$ is limited to the upper ceiling 1.0 (i.e. $1-\text{puv}^U$ is fixed to 0 when the accumulated UV dose exceeds the limit of safe UV dose).

Figure 3:
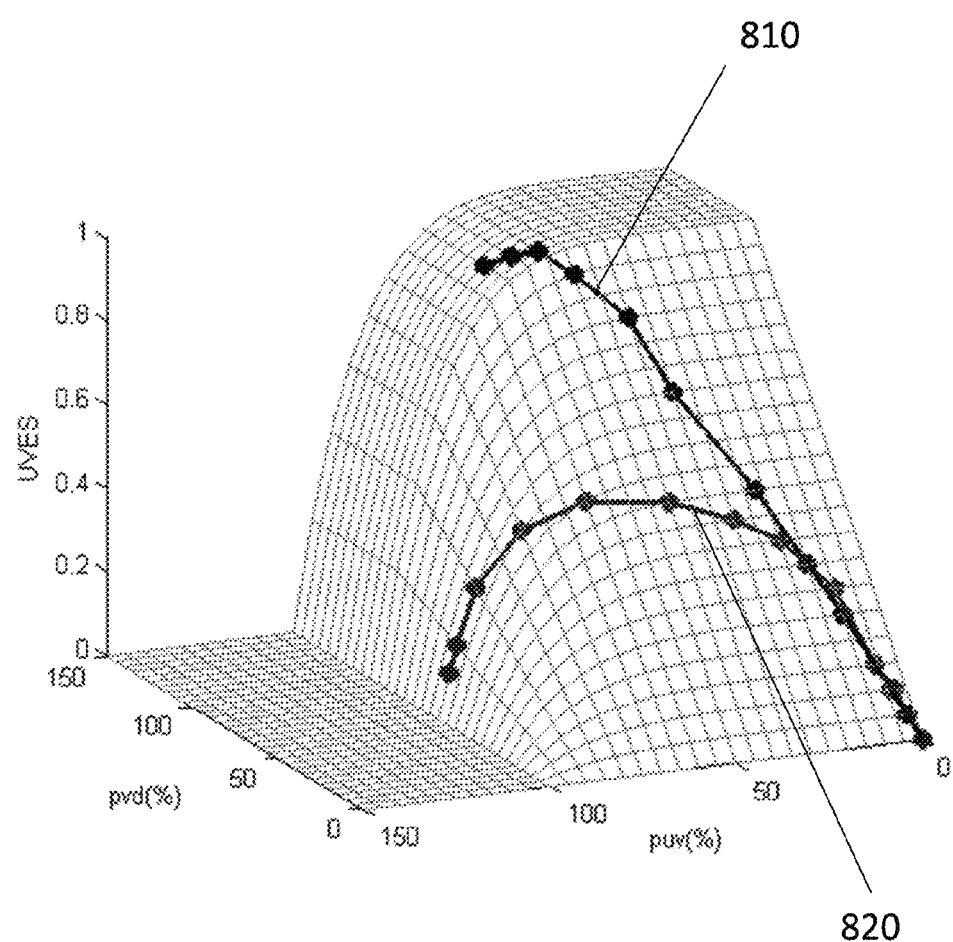
FIG. 3 shows the 3D view of UV exposure score (UVES) as a function of pvd (percentage of vitamin D production toward the user-defined daily goal) and puv (percentage of accumulated UV dose against the limit of safe UV dose).

For the purpose of illustration, FIG. 3 shows the 3D view of UVES as a function of pvd and puv. Alternatively, a 2D view of UVES can be displayed in grey scale or color-coded. As examples, two simulated trajectories of accumulated UV dose and amount of vitamin D production over a period of time are also shown. As can be seen, while one trajectory 810 progressively reaches the optimal state (high UVES)—evidenced by exceeding the goal of vitamin D production (pvd>100%) and not reaching limit of safe UV dose (puv<100%), the other trajectory 820 fails to climb to the optimal state—the vitamin D production is less than 70% of the daily goal, and the accumulated UV dose is near the limit of safe UV dose. Therefore, the composite metric UVES provides a quantitative means to characterize the degree of balance between the benefit and risk of UV exposure. Users can use this metric as a guidance to optimize their sun exposure. In addition, daily log of the UVES can provide a historical view and trending analysis of the overall sun exposure experience.

An alternative metric is termed UV balance index (UVBI), which ranges from −1 to 1. More negative UVBI (approaching −1) indicates lower vitamin D production, whereas more positive UVBI (approaching 1) indicates higher risk of sunburn (obviously, it is equivalent to define UVBI using the opposite form −UVBI, so that more positive value indicates lower vitamin D production, whereas more negative value indicates higher risk of sunburn). The optimal balance of UV exposure is reflected by UVBI value that is close to zero. Unlike UVES, UVBI can differentiate two sub-optimal UV exposure conditions (low production of vitamin D vs. high risk of sunburn). As an example, UVBI can be defined as:

$$\text{UVBI} = (1 - \text{puv}^U)(\text{pvd}^V - 1) + W \cdot \text{puv}^U \quad (2)$$

where W is a weighting function that as described below. Similarly, pvd is the percentage of vitamin D production toward the daily goal, puv is the percentage of accumulated UV dose against the limit of safe UV dose, and V and U are two positive parameters that can be predefined or programmed by the user. Likewise, both $\text{pvd}^V$ and $\text{puv}^U$ have the upper ceiling of 1.0.

Note the first term $(1-\text{puv}^U)(\text{pvd}^V-1)$ approaches 0 when either $\text{puv}^U$ or $\text{pvd}^V$ approaches 1, thus UVBI will be determined by the second term $W \cdot \text{puv}^U$ in these two conditions. The weighting function W can be user defined such that it satisfies the following criteria:

(a) If puv approaches or exceeds 1 ($\text{puv}^U \to 1$), then UVBI approaches 1.

(b) If puv is sufficiently smaller than 1 ($\text{puv}^U < 1-\epsilon$, where $0 < \epsilon < 1$) AND pvd approaches or exceeds 1 ($\text{pvd}^V \to 1$), then UVBI approaches 0.

(c) Otherwise, UVBI approaches −1 as pvd approaches 0 ($\text{pvd}^V \to 0$).

One exemplary definition of the weighting function is to set W=0 if condition puv<0.85 OR (puv<1 AND pvd<0.75) is met, or set W=puv otherwise. Another exemplary definition of the weighting function is to set W=0 if condition puv<0.75

OR ($puv^2+pvd^2<1.44$ AND $pvd<0.9$) is met, or set W=puv otherwise. The purpose of conditional setting W to zero is to avoid or minimize the effect of numerical cancellation between the first and second terms in equation (2). Clearly, the weighting function can be defined by many other means as long as the three criteria described above are met.

Calculation of Safe Sun Exposure Time

For a wearable UV dosimetry system, an essential feature is to predict how long the user can safely stay exposed to sun light before getting sun burn. The time to skin burn is a dynamic parameter. It is affected by the time varying intensity of UV irradiance. It also depends on the accumulated UV dose already received by the user. Moreover, it can be modified by the user's behaviors, such as seeking the shade, changing clothing coverage, applying the sunscreen, etc. This section describes a method for dynamic estimation of the safe sun exposure time in a UV dosimetry system.

The UV sensor embedded in the UV sensing unit generates output of UV intensity (unit: $J/m^2$) over time, which can be represented as a time series that has the sampling interval $T_s$. The device then calculates the accumulated UV dose by integrating the UV intensity over time based on the trapezoidal rule.

$$D(t) = \left[\sum_{k=0}^{t}(I_k + I_{k+1}) \cdot (t_{k+1} - t_k)\right]/2 \quad (3)$$

where D(t) is the accumulated dose from predefined time 0 until time t, $I_{k+1}$ and $I_k$ are respective UV intensity readings at two consecutive sample times $t_{k+1}$ and $t_k$. The accumulated UV dose and the time are reset at predefined time of day. For example, the elapsed time is typically reset to 0 at midnight, and the accumulated UV dose is cleared at the time reset.

Typically, $t_{k+1}-t_k=T_s$ when all regularly sampled data are available, but the time gap may be greater than $T_s$ in case of missed data, e.g. due to data loss during wireless transmission or rejection of invalid data due to measurement noise. When the time gap is greater than a predefined threshold $\Delta$, the UV intensity can be assumed to be zero within the time gap. Alternatively, the UV intensity can be assumed to remain the same as the last valid sample. Yet another alternative is to assume the UV intensity gradually decrease from the last valid sample to zero in a linear or nonlinear fashion.

Assuming there is no additional protection (e.g. sunscreen use or clothing coverage) for the skin area near the UV sensing unit, the safe sun exposure time can be expressed in terms of time to skin burn (T2SB), which is defined as:

$$T2SB=[p \cdot MED-D(t)]/b \quad (4)$$

where p is a positive coefficient that is user-programmable, MED is the predefined minimal erythemal dose that is dependent on user's skin type according to the Fitzpatrick scale, and b is the projected slope of UV dose accumulation.

Figure 4:
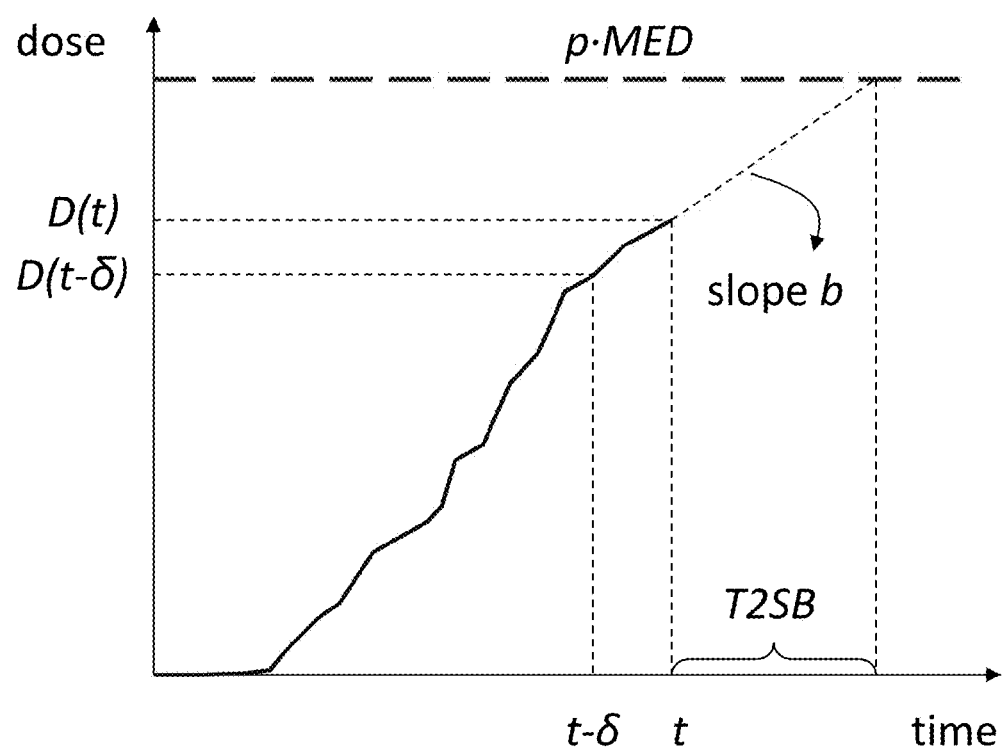
FIG. 4 illustrates the concept of estimating the slope of UV dose accumulation based on linear regression of the most recent UV dose accumulation curve.

Note the product p·MED defines the maximum UV dose that is considered safe for the user, where the parameter p allows user to specify the scale in terms of MED that the user can tolerate. For example, the maximum safe UV dose is 1 MED when p=1, or 1.5 MED when p=1.5, or 0.9 MED when p=0.9. As illustrated in FIG. 4, the projected slope of UV dose accumulation may be obtained based on the linear regression of the most recent UV dose accumulation curve. Denote T the time vector ranging from time t–δ to time t, and D the UV dose vector ranging from D(t–δ) at time t–δ, to D(t) at time t, where δ can be a predefined constant or a user-programmable parameter, then the projected slope b is calculated as:

$$b=[N\Sigma(D \cdot T)-(\Sigma D)\cdot(\Sigma T)]/[N(\Sigma T^2)-(\Sigma T)^2] \quad (5)$$

where N is the total number of samples between time t–δ and time t (note: each sample has a pair of sample time and UV dose value).

Two special cases need to be considered when t<δ (i.e. at the beginning of the day, shortly after the midnight) or when D(t)–D(t–δ)=0, which means there is no UV exposure in the past δ duration, hence the slope b=0 (i.e. the UV dose segment is flat). In such cases, the projected T2SB is infinite.

Figure 5:
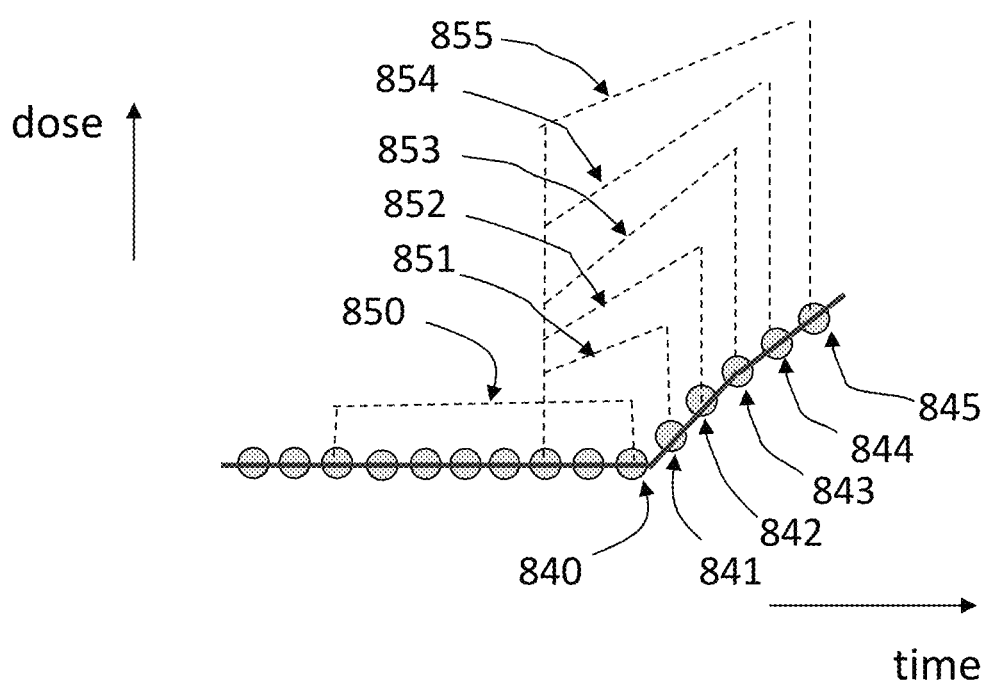
FIG. 5 illustrates the concept of adjusting vector length for calculating the slope of UV dose curve that has a flat segment followed by an upward increase.

If the UV dose increases after a flat segment, equation (5) can be similarly used to calculate the new slope. However, the vector length of T and D are reduced, and then they gradually increase until reaching the full length N. This can be illustrated in FIG. 5, which shows a portion of UV dose curve with a flat segment followed by an upward increase. In this example, each sample of UV dose curve (solid line) is marked by a circle. The UV dose curve remains flat until its last sample 840. Then the UV dose curve starts to increase from sample 841. For illustration purpose, the vector length N is set to 8 in this example. The slope b remains zero throughout the flat segment, including its last 8 samples 850. Upon detecting an increase of the UV dose at sample 841, the vector length is reduced to 4 in this example. Thus the slope is evaluated using only a group of 4 samples 851. As new UV dose values are available after sample 841, the vector length starts to increase toward its original length (N=8). As illustrated in the figure, for the sample 842, the slope is evaluated using a group of 5 samples 842; for the sample 843, the slope is evaluated using a group of 6 samples 843; for the sample 844, the slope is evaluated using a group of 7 samples 854; and for the sample 845, the slope is evaluated using a group of 8 samples 855. This adaptive adjustment of vector length for calculating slope is important because while the linear regression allows smooth projection of T2SB (i.e. noise tolerant), shortening vector length after a flat segment allows quick adaptation of rising UV dose curve after sudden exposure to sunlight.

Yet in another embodiment, the projected slope of UV dose accumulation is based on the current or recent UV intensity, instead of based on linear regression analysis of the UV dose accumulation curve. Specifically, the projected slope of UV dose accumulation is the product of UV intensity (I) and the sampling interval ($T_x$), i.e. $b=I \times T_s$. This assumes that the UV intensity remains the same for the foreseeable near future. In one example, I is the device measured current UV intensity. In another example, I is the extrapolated UV intensity value based on the most recent measurement of UV intensity in a short time window. The method of calculating the extrapolated UV intensity value in a short time window is described below in the section titled "Extrapolation of UV Sensor Output". Yet in another example, I is the forecasted or crowd sourced UV intensity value that is time and location specific to the user. This is useful when the user is staying indoor or in the shade but wants to have a rough estimate of T2SB should he or she goes outside to get exposed to sunlight, without actually measuring the UV intensity using the device.

When the UV sensor is not aligned with the direct solar irradiance, measurements may understate the UV intensity at surface that is normal to the sun light. Therefore, the measured UV intensity, as well as the calculated accumulated UV dose D(t) will vary depending on where the UV sensing unit is worn (or maybe the sensor is just located nearby but not worn on the body). There are many variables affecting the UV irradiance angle, such as the solar zenith angle, the orientation and body movement of the subject, and the environment surrounding the subject (e.g. shade, light reflections, etc). While it may be impractical to account for all these factors in real time, scaling the sensor measured UV intensity or dose by a sensor location factor (SLF) may provide a reasonable estimate of the UV intensity or D(t) at different body surface areas. For example, if the UV sensor is worn on user's wrist facing outward, the sensor measured UV dose at the wrist will need to be multiplied by a site-specific SLF to derive the UV dose at an uncovered body area, such as the face, shoulder, chest, legs, etc. The determination of SLF at different body parts is ideally through a calibration phrase, when a plurality of UV sensors are worn by the user at different locations for a certain period of time, and the ratios between UV dose readings from these sensors are used to determine site-specific SLF. Typically, default values of SLF for different sensor locations can be predefined based on an experimental study involving a group of subjects. Similar approach is described in the paper authored by Thieden et al. "The wrist is a reliable body site for personal dosimetry of ultraviolet radiation." Photodermatol Photoimmunol Photomed 2000; 16: 57-61. As expected, a user may experience skin burn earlier on the face or shoulder than on the arms or legs because the actual UV dose varies among different body parts. Therefore, the safe sun exposure time T2SB will depend on which part of the body surface is uncovered, and is calculated based on the highest accumulated UV dose D(t) that is adjusted for SLF.

Another factor that affects the safe sun exposure time is the topical application of sunscreen. Usage of sunscreen with high skin SPF can significantly block or absorb UV radiation, thus prolong the time to skin burn (T2SB). In general, for an uncovered skin area with adequate sunscreen application, the safe sun exposure time calculated above is adjusted by multiplying the SPF of the sunscreen. Thus, if the calculated T2SB without sunscreen is 10 minutes, then the safe sun exposure time will be 150 minutes after proper application of sunscreen with the SPF 15. Note, however, the effective SPF is not only dependent on the product labeling, but also the frequency and amount of sunscreen applied, the binding property of the sunscreen, the elapsed time since last sunscreen application, and so on. The method for calculating effective SPF is described below in the section titled "Calculation of Effective SPF".

Calculation of Cutaneous Vitamin D Synthesis

A UV dosimetry system that can calculate the daily vitamin D production resulting from solar UV exposure will provide useful information for the user to determine if vitamin D supplement is necessary, and if so, how much is necessary. Such quantitative information will offer user objective guidance to achieve optimal balance of sun exposure, and prescribe behavioral changes in maintaining personal health. This section describes a method for calculating daily vitamin D production from UV light in a UV dosimetry system.

The formula for calculating the amount of vitamin D produced by people from an average daily UV exposure was originally described by Godar et al. (Environ Health Perspect 2012; 120:139-143). Instead of relying on average UV dose derived from a sample population, more accurate estimation of individual's daily cutaneous vitamin D synthesis (DVD) due to UV exposure can be obtained by integrating the subject's instantaneous vitamin D production rate over a day using the trapezoidal rule:

$$DVD = \sum_k [(V_k + V_{k+1}) \cdot (t_{k+1} - t_k)]/2 \qquad (6)$$

where $V_{k+1}$ and $V_k$ are respective vitamin D production rate at two consecutive sample times $t_{k+1}$ and $t_k$. The DVD and time are reset at predefined time of day. For example, the elapsed time is typically reset to 0 at midnight, and DVD is cleared at the time reset and accumulates over 24 hours. Obviously, vitamin D production over different time intervals (e.g. hourly, etc.) can be similarly calculated. Typically, $t_{k+1}-t_k$ equals the device sampling interval when all regularly sampled data are available, but the time gap may be greater than the sampling interval in case of missed data, e.g. due to data loss during wireless transmission or rejection of invalid data due to measurement noise. When the time gap is greater than a predefined threshold $\Delta$, the vitamin D production rate can be assumed to be zero within the time gap. Alternatively, the vitamin D production rate can be assumed to remain the same as the last valid sample. Yet another alternative is to assume the vitamin D production rate gradually decrease from the last valid sample to zero in a linear or nonlinear fashion.

At any given time instant, the vitamin D production rate (V) is calculated as:

$$V = C \cdot cf \cdot sf \cdot af \cdot bf \cdot \sum_s (I_s \cdot pBSA_s/eSPF_s) \qquad (7)$$

where C=49 is a constant which is derived from a reference value corresponding to the approximate amount of vitamin D generated (measured in ×100 IU) by a typical young female subject having Fitzpatrick skin type II with a whole body exposure to nearly uniform UV irradiance at the intensity of 320 J/m$^2$. As described in details below, cf is the action spectrum conversion factor, sf is the skin type factor, of is the age factor, and bf is the body surface area factor. The summation term represents the total contribution of vitamin D production from all exposed body surface area, which is divided into multiple parts (e.g. face, chest, arms, legs, etc). For each part of exposed body surface area (s), the corresponding UV intensity ($I_s$), its percentage of total body surface area ($pBSA_s$), and the effective sun protection factor ($eSPF_s$) of the applied sunscreen are considered for the calculation.

The action spectrum conversion factor cf changes erythemally weighted to previtamin D3 weighted UV doses. For general calculation, cf can be simplified to be a constant 1.0, that is, the differences between wavelength contributions estimated by the erythmal action spectrum and the previtamin D action spectrum are ignored. Alternatively, cf can be determined by linear interpolation of values reported by Pope et al (Photochem Photobiol 2008; 84:1277-1283), by taking into account of season and the user's latitude.

Increased skin pigment can greatly reduce the capacity of skin to synthesize vitamin D. Thus the UV dose required to make the same amount of vitamin D varies by skin type. Using Fitzpatrick skin type II as the reference, the skin type factor sf can be determined, as described by Godar et al. (Environ Health Perspect 2012; 120:139-143), based on the respective minimum erythmal dose (MED) values.

It has also been known that aging significantly affects the capability of human skin to produce vitamin D. Compared to a 20 years old adult, a 70 years old person has about 75% reduced capacity to make vitamin D in the skin. The age-dependent capability of vitamin D production can be characterized by age factor af which can be fixed to 1.0 for age<20 years and 0.10 for age>80 years, and decreases following a linear model for age between 20-80 years:

$$af=1-0.015 \cdot (age-20) \qquad (8)$$

The amount of vitamin D production in a person depends on how much skin is exposed to UV light. Given the same percentage of skin area exposure, a person with a larger body surface area (BSA) will produce more vitamin D than a person with a smaller BSA. The body surface area factor bf is the ratio of a person's BSA to 1.7 m², which is approximately the BSA of a typical female subject. A person's BSA can be calculated based on the formula of DuBois and DuBois. Hence the body surface area factor bf is calculated as:

$$bf = 0.20247 \times H^{0.725} \times W^{0.425}/1.7 \quad (9)$$

where the person's height (H) is in meters and weight (W) is in kilograms.

Only skin surface exposed to UV light can synthesize vitamin D. The total BSA can be divided into different parts, for example, based on the Lund and Browder chart, which specifies the approximate percentage of each part's surface area relative to the total BSA. Different clothing choices can affect the percentage of body surface area that is exposed. Specification of various body parts and their corresponding percentages of body surface area corresponding to common clothing choices are described in the following section titled "Calculation of Exposed Body Surface Area".

In a simplified scenario, the UV intensity measured by the wearable UV sensor is assumed to be uniform over the exposed body surface, and the sunscreen application is also assumed to be uniform. Then equation to calculate the vitamin D production rate can be simplified to:

$$V = C \cdot cf \cdot sf \cdot af \cdot bf \cdot I \cdot pBSA/eSPF \quad (10)$$

where I is the UV intensity, pBSA is the percentage of total BSA being exposed to UV light, and eSPF is the effective SPF of the applied sunscreen. Note the effective SPF is not only dependent on the product labeling, but also the frequency and amount of sunscreen applied, the binding property of the sunscreen, the elapsed time since last sunscreen application, etc. The method for calculating eSPF is described below in the section titled "Calculation of Effective SPF".

Also note that the measured UV intensity at the sensor wearing location may be different from the actual UV intensity at a different body area due to varying solar irradiance angle. As described above in the section titled "Calculating of Safe Sun Exposure Time", scaling the sensor measured UV intensity by a sensor location factor (SLF) may provide a reasonable estimate of the UV intensity at different body surface areas, and the SLF at different body parts can be determined through a calibration phrase. As another example, a user may apply sunscreen over some, but not all exposed body surface areas. Thus the eSPF at different parts of body surface may vary significantly.

Knowing the vitamin D production rate (V) and the daily goal of vitamin D amount (DGVD) which can be programmed by the user, the device can also estimate the time remaining to reach the DGVD (T2VD). Specifically, at any time of the day, T2VD can be calculated by dividing the difference between DGVD and the accumulated vitamin D production at that time by a projected slope of vitamin D accumulation. This calculation can be performed in a way that is similar to the method of calculating the time to skin burn (T2SB) as described above in the section titled "Calculation of Safe Sun Exposure Time". For example, at any time of the day, the device can calculate the projected slope of vitamin D accumulation based on linear regression analysis of accumulated vitamin D production curve in the preceding time interval. Alternatively, the device can set the projected slope of vitamin D accumulation to the product of sampling interval and the vitamin D production rate (V). The vitamin D production rate (V) can be calculated using equations (7) or (10), where the UV intensity can be currently measured value, or the extrapolated value based on the most recent measurement of UV intensity in a short time window. The method of calculating the extrapolated UV intensity value in a short time window is described below in the section titled "Extrapolation of UV Sensor Output". Yet in an alternative embodiment, the vitamin D production rate (V) is calculated based on the forecasted or crowd-sourced UV intensity value that is time and location specific to the user. This could be useful when the user is staying indoor or in the shade but wants to have a rough estimate of T2VD should he or she goes outside to get exposed to sunlight, without actual measuring the UV intensity using the device.

Calculation of Effective SPF

As noted above, the effective SPF of a sunscreen product often actually deviates from the labeled SPF, due to some common factors including the amount of sunscreen initially applied, binding property of the sunscreen, reapplication of the sunscreen, and time elapsed since previous sunscreen application, etc. This section describes a method for calculating the effective SPF in a UV dosimetry system.

After initial application of sunscreen, it is removed from the skin by clothing or sweating such that the thickness remaining on the skin decreases with time in an exponential manner. This can be mathematically modeled by:

$$x(t) = x(0) \cdot \exp(-\lambda t) \quad (11)$$

where x(t) is the sunscreen thickness at time t, x(0) is the initially applied sunscreen thickness, λ is rate constant for sunscreen removal that is related to the substantivity half-life of the sunscreen, which characterizes the binding capability of the sunscreen, and can be approximately determined based on such factors as the type of sunscreen, and the activity of the subject (toweling, sweating, swimming, etc.). When sunscreen is reapplied at time T, the newly applied sunscreen amount α is added to the remaining sunscreen x(T), and the time course of sunscreen thickness follows the same exponential curve for t>T.

The relationship between sunscreen application thickness and the resulting SPF has been investigated by a number of studies. The results have been variable ranging from an exponential relationship between SPF and applied thickness, to a logarithmic relationship, and through to an approximately linear relationship. Depending on the spectral absorption profile of the product, the relationship could vary. For example, a linear relationship of the SPF and the sunscreen application thickness can be modeled by:

$$SPF_E = 1 + (SPF_L - 1) \cdot x/2 \quad (12)$$

where $SPF_E$ denotes the effective SPF, $SPF_L$ is the labeled SPF of the sunscreen product, and x is the sunscreen thickness which can be calculated from equations described above. Based on this model, the sunscreen achieves its labeled SPF value when the application amount is 2 mg/cm² as specified in the international protocol. The unit intercept on SPF axis implies no additional sun screen protection when no sunscreen is applied (i.e., x=0).

Calculation of Exposed Body Surface Area

To estimate the amount of cutaneous vitamin D synthesis, it is important to calculate the percentage of exposed body surface area, taking into account of various options of clothing coverage. This section describes the method to calculate the exposed body surface area in a UV dosimetry system.

A person's total body surface area (BSA) can be calculated using the DuBois and DuBois formula.

$$BSA = 0.20247 \times H^{0.725} \times W^{0.425} \quad (13)$$

where the person's height (H) is in meters and weight (W) is in kilograms. The total BSA can be divided into different body parts based on the Lund and Browder chart, which specifies the approximate percentage of each part's surface area relative to the total BSA and is known to be age dependent.

Age is a main factor affecting the percentage values in the Lund and Browder chart because the ratio of the surface area of the head to the surface area of the limbs is typically larger in children than that of an adult. To estimate the surface area of various body parts different ages, linearly interpolated values can be found between ages on the Lund-Browder charts.

Different clothing choices can affect the percentage of total BSA that is exposed. The UV dosimetry system may allow user to select different clothing combinations for different parts of the body by browsing through or toggling between various clothing options. For example, the user can toggle between "with hat" and "no hat" to indicate coverage or exposure of head. Likewise, the user can select "bare chest", "short sleeve", or "long sleeve" to represent different degrees of upper body coverage. Clothing coverage for other parts of the body surface can be similarly defined. The selection of clothing options can vary in number and styles. Each selected clothing option can have a predefined surface area coverage percentage for the selected body part.

A lookup table can be predefined that lists the approximate percentage values of skin exposure of various body parts as a result of common clothing choices. An empty cell in the table indicates the skin surface of the body part (e.g. in the row) is not affected by the corresponding clothing option (e.g. in the column) In contrast, a value of zero in the cell means no skin exposure for the corresponding body part, i.e. it is completely covered by the clothing. To calculate the percentage of a person's exposed BSA relative to the total BSA, each body part's BSA percentage (obtained from the Lund and Browder chart) is multiplied by the body part's skin exposure percentage value based on the corresponding clothing choice, and then these weighted terms are summed.

Extrapolation of UV Sensor Output

While it is common sense that the UV sensor should not be obstructed from the sun for accurate measurement, in practical use the device may experience changing angle of the irradiating sunlight and/or temporary shading of the device. The design of a UV dosimetry system shall take this variability into account, to at least partially compensate for the body movement and temporary obstruction of the UV sensor. This section describes a method to filter out the unreliable UV measurement in a UV dosimetry system based on signal processing of the sensor generated UV intensity data.

The UV sensor embedded in the UV dosimetry system generates real time output of UV intensity. To estimate the actual UV intensity irradiated on the subject, the UV intensity measured by the UV sensor can be extrapolated by means of statistical analysis of the data, based on two basic assumptions:

(1) The actual UV intensity received by the subject is quasi-static, that is, the rate of change of UV intensity irradiated on the subject is slow over a short duration.

(2) When the subject is exposed to the sunlight, the wearable UV sensor will have proper alignment with the solar irradiance at least for a very brief period of time during the short duration when actual UV intensity is stable.

Therefore, although the wearable UV sensor may often measure lower than actual UV intensity due to the changing body position and/or shade coverage, as long as the user is non-stationary so that the sensor can have good alignment with the sunlight from time to time, even if briefly, the device may have correct or nearly correct measurement of the actual UV intensity. On the other hand, it is important to note that even though the sensor measured UV intensity is below the actual value, the underestimation may be limited since it is likely that not all exposed body surface is normal to the sunlight. In other words, part of the exposed body surface may indeed receive less UV exposure due to its non-normal orientation and/or shade coverage.

Figure 6:
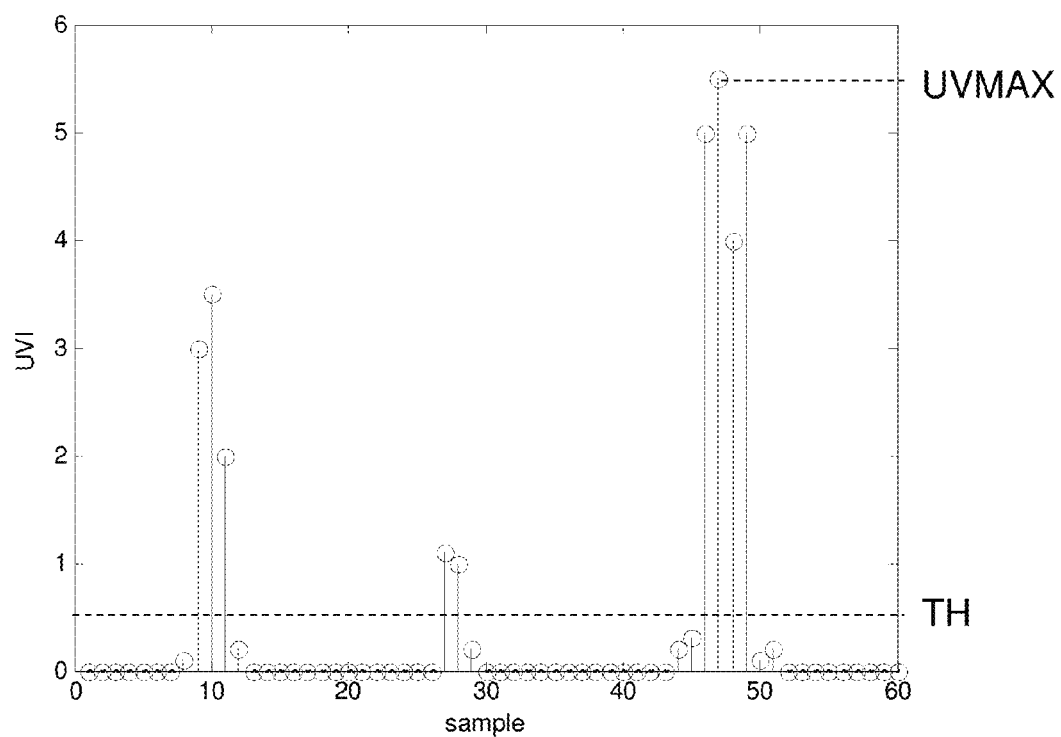
FIG. 6 illustrates that the actual UV intensity irradiated on the subject over a short period of time can be extrapolated based on the limited numbers of correct measurement of UV intensity obtained during that short time window.

Based on the above assumptions, the actual UV intensity irradiated on the subject over a short period of time can be extrapolated based on the limited numbers of correct measurement of UV intensity obtained during that short time window. The extrapolation method is described below with reference to FIG. 6.

Assume the device measures M samples of UV intensity values over a short time window T (e.g. T=60 s, corresponding to M=60 for a sampling frequency of 1 Hz). Data extrapolation performed in this time window (as described below) will be repeated for the next time window, which can be overlapping or non-overlapping with the current time window. A programmable UV intensity threshold TH (e.g. 0.5 UVI, or 12.5 mW/m$^2$) defines the boundary above which the measured UV intensity is likely more representative of the actual value whereas below which the sensor output is likely an underestimate of the true UV intensity. Further denote the maximal UV intensity value among the M samples is UVMAX, which is assumed to be obtained when the sensor is best aligned with the solar irradiance during the short time window T. Also, when the device comprises multiple UV sensors that measure the UV intensity at different angles, the UVMAX can be taken as the maximum UV intensity value measured by all UV sensors during the short time window.

The device counts the number of samples (G) in the short window T that have measured UV intensity greater or equal to the threshold TH. Higher count of G indicates higher probability and confidence that the measured ≥TH values reflect the true UV intensity whereas smaller G implies vice versa. The count G is compared to another predefined thresholds C (e.g. C=8 for M=60). If the count G is greater than 0 (i.e. at least one sample of measured UV intensity is above TH), then the extrapolated UV intensity of all M samples in the short time window T is set to $$\text{MIN}(G,C)/C \times \text{UVMAX}$$

where MIN( ) is the function that returns the minimum value. In other words, the extrapolated UV intensity of all M samples is set to UVMAX if G≥C. If 1<G<C, then the extrapolated UV intensity of all M samples is set to a fraction of the UVMAX, in proportion to the count G. On the other hand, if G=0 (i.e. no sample has measured UV intensity above TH), then the extrapolated UV intensity values of the M samples remain unchanged from the measured UV intensity values.

Calculation of Sun Exposure Time

This section describes a method for calculating the daily sun exposure time (SET) in a UV dosimetry system. This feature may not only reveal the likely correlation between a user's mood and SET, but also provides the user guidance to enhance mood by consciously adjusting SET.

The UV sensor embedded in the wearable device generates output of UV intensity over time which can be converted to the time series of UV index (UVI). The daily SET is defined as the total duration of the day when the sensor measured UVI is greater than a predefined lower threshold ($UVI_{LT}$).

Denote UVI1 and UVI2 the respective UVI readings of the device at two consecutive time points t1 and t2 (t2 >t1). Further denote dt the duration between t1 and t2 that contributes to SET, which is the time period between t1 and t2 when UVI is greater than or equal to $UVI_{LT}$. Based on the values of UVI1 and UVI2, dt can be calculated according to different conditions: (1) dt=0 if both UVI1 and UVI2 are less than $UVI_{LT}$ (i.e. no sun exposure between t1 and t2); (2) dt=t2 −t1 if both UVI1 and UVI2 are greater than or equal to $UVI_{LT}$ (i.e. continuous sun exposure between t1 and t2); (3) dt is calculated as a fraction of the duration between t1 and t2 based on linear interpolation if UVI1 is below while UVI2 is above $UVI_{LT}$, or if UVI2 is below while UVI1 is above $UVI_{LT}$. Yet in a simpler version, the calculation of dt in condition (3) above can be approximated as (t2 −t1)/2. This is appropriate when sampling interval is sufficiently small.

During normal operation, the device resets SET to zero at midnight, and accumulates dt into SET anytime when device measured UVI is greater than or equal to $UVI_{LT}$ until the end of the day. Typically, the device measures the UV intensity and converts it to UVI at the sampling interval. However, the time gap between two consecutive measurements may be greater than the sampling interval in case of missed data, e.g. due to data loss during wireless transmission or rejection of invalid data due to measurement noise. When the time gap is greater than a predefined threshold Δ, the UVI may be assumed to be zero within the time gap. Alternatively, the UVI can be assumed to remain the same as the last valid sample. Yet another alternative is to assume the UVI gradually decrease from the last valid sample to zero in a linear or nonlinear fashion.

Method to Predict Optimal Sun Exposure Time

While it is helpful for a person to obtain instant feedback on received UV dose and cutaneous vitamin D production, and use such information as a guidance to optimize sun exposure, more benefits can be gained if the person can plan ahead for optimal sun experience. This section describes a method for predicting the effects of sun exposure to the user in the next few days in a UV dosimetry system.

Figure 7:
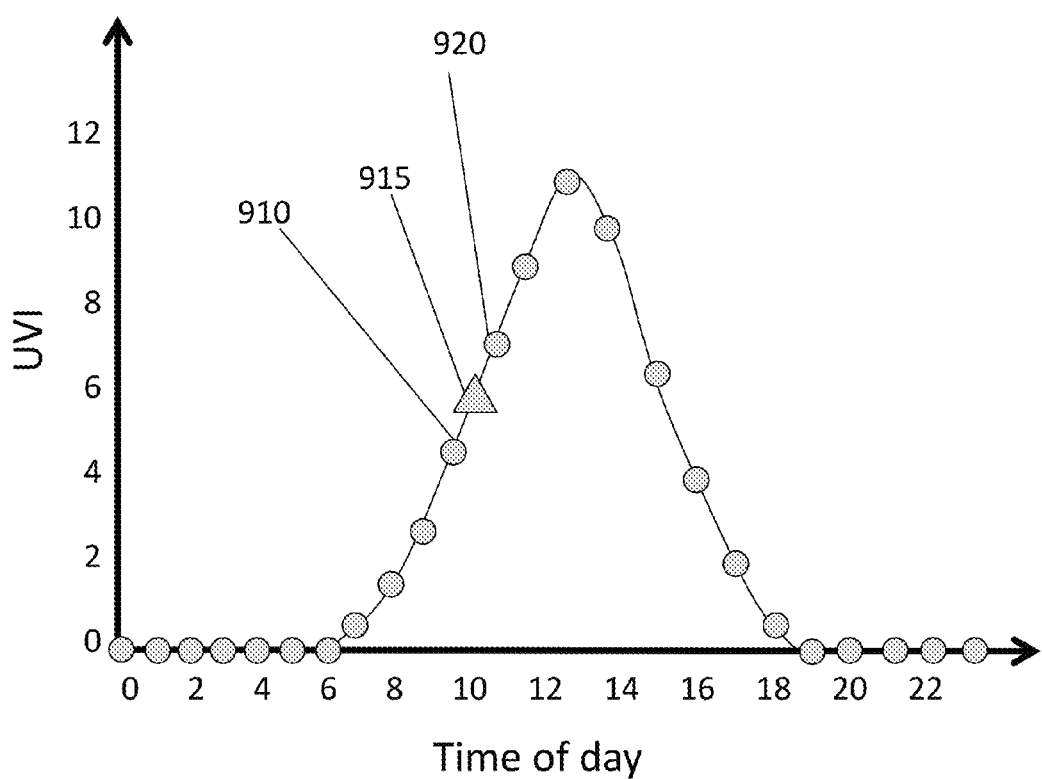
FIG. 7 illustrates the concept of temporal interpolation of UVI or UV intensity at any given time of day based on the forecast UVI data.

According to a preferred embodiment of this invention, the UV dosimetry system retrieves forecasted UVI data for the next few days corresponding to the user's location from trusted sources or official websites, e.g., www.epa.gov, www-.weather.gov, etc. The user's location can be automatically determined via GPS integrated in the mobile computing device of the UV dosimetry system. In addition, the user's location can be specified by the user through the input interface of the UV dosimetry system. This is helpful if the user plans to travel to a different location and wants to predict the effects of sun exposure at the new location. The forecasted UVI data often has limited temporal and spatial resolution. For example, the forecasted UVI data is often presented hourly, and it is only presented for selected cities and/or areas associated with certain zip codes. To overcome this challenge, linear or nonlinear (e.g. spline) interpolation can be used to obtain forecasted UVI data at specific time and location with higher resolution. For example, FIG. 7 illustrates the concept of temporal interpolation of UVI data. In this example, the forecast 24-hour UVI data is available for a specific location. While the forecast data is only available hourly (labelled in circles), the UVI or UV intensity at any given time of day 915 (labelled in a triangle) can be interpolated between UVI values of adjacent time points 910 and 920. Since 1 UVI corresponds to UV intensity of 25 $mW/m^2$, the interpolated UV intensity (which can be expressed in continuous values) is preferred than interpolated UVI (which can only be expressed in discrete values). For spatial interpolation of UVI, a geographic map can be generated with a specified latitude-longitude grid which has a high spatial resolution. The UVI at a specific target location without forecast data can be interpolated from neighboring grid points that have forecast UVI data available. Therefore, the UV dosimetry system can predict UV intensity at specific location and given time of day by means of interpolation of the forecast UVI data.

According to one embodiment of this invention, the UV dosimetry system estimates the user received UV dose and generated vitamin D in the near future (e.g. next day) based on the predicted UV intensity data for a plural of hypothetical UV exposure scenarios. Each hypothetical UV exposure scenario corresponds to a combination of start time and duration of UV exposure, and the corresponding user characteristics such as the clothing coverage, sunscreen usage, and wearing location of the UV sensing unit. These hypothetical scenarios can be predefined by the user, or can be edited by the user through the user interface of the portable computing device. For example, the user can predefine the scenarios based on his/her past habit or routine of UV exposure, or add/delete/modify the scenarios arbitrarily, e.g. 20 minutes sun exposure starting at 9 am, 10 minutes sun exposure starting at 10 am plus 5 minutes exposure starting at 12 noon, etc. The user characteristics (e.g. clothing coverage, sunscreen usage, and wearing location) associated with each episode of UV exposure can be predefined or edited by the user. Therefore, for each of the hypothetical UV exposure scenarios, the UV dosimetry system can estimate the corresponding UV dose received by the user and vitamin D production. The method of calculating the accumulated UV dose is described above in the section titled "Calculation of Safe Sun Exposure Time", and the method of calculating vitamin D production is described above in the section titled "Calculation of Cutaneous Vitamin D Synthesis." Based on the estimated UV dose and vitamin D production, the UV dosimetry system can evaluate the composite metric UVES and/or UVBI for each of the hypothetical UV exposure scenarios as described above in the section titled "Optimal Balance of UV Exposure". Consequently, the UV dosimetry system can provide the user a ranked list of hypothetical UV exposure scenarios based on the calculated composite metric UVES and/or UVBI, such that the scenario ranked high on the list is more preferred (i.e. more balanced with respect to the risk of sun burn and benefit of vitamin D production) than the scenario ranked low on the list, and the user can use such a ranked list as a guide to plan ahead for future sun exposure.

According to another embodiment of this invention, the UV dosimetry system can estimate the safe sun exposure time, the amount of vitamin D generated during the safe sun exposure time, and the duration of sun exposure needed to reach user-defined daily goal of vitamin D production, for a plural of hypothetical UV exposure scenarios. Different from the embodiment described above, each hypothetical UV exposure scenario corresponds to a start time of UV exposure, and the corresponding user characteristics (e.g. clothing coverage, sunscreen usage, and wearing location of the UV sensing unit), but the duration of UV exposure is not defined. Similarly, these hypothetical scenarios can be predefined by the user, or can be edited by the user through the user interface of the portable computing device. For each of the hypothetical UV exposure scenarios, the UV dosimetry system estimates the safe sun exposure time (e.g. time to sun burn), the amount of vitamin D generated during the safe sun exposure time, and the duration of sun exposure needed to reach user-defined daily goal of vitamin D production. For example, the UV dosimetry system may estimate for one scenario, the user will have 20 minutes safe sun exposure time, generate 800 IU of vitamin D during that period, and need only 10 minutes of sun exposure to reach the user-defined daily goal of 400 IU vitamin D. Thus the user can plan to enjoy the sun exposure, knowing he/she will get enough vitamin D before having the risk of sunburn in this scenario. In another scenario, the UV dosimetry system may estimate that the user will have only 10 minutes of safe sun exposure time, generate 500 IU of vitamin D during that period, and will need 25 minutes of sun exposure to reach the user-defined daily goal of 1000 IU vitamin D. Thus the user can plan to limit the sun exposure time and take vitamin D supplement for this scenario. Similarly, the method of calculating the safe sun exposure time is described above in the section titled "Calculation of Safe Sun Exposure Time", and the method of calculating vitamin D production is described above in the section titled "Calculation of Cutaneous Vitamin D Synthesis."

Method for Crowd Sourcing of UVI Data

According to this invention, UVI at various geographical locations is measured and updated in real-time by a large number of UV measurement devices, or UV meters, by means of crowd sourcing method. People who are using UV meters such as the disclosed UV dosimetry system, are encouraged to provide the real-time UVI data together with the time (e.g. using the build-in clock of the mobile device) and location information (e.g. via GPS embedded in the mobile computing device) through the wireless network to a remote server, for example, in exchange for a credit or discount coupon to be used toward certain products or services. Users who opt to provide data can be anonymous to protect their identities.

The remote server maintains a database containing the data transmitted from the UV meters. A user "pushes" the measured data (UVI, time, location) to the remote server in triggered mode, automatic mode, or mixed mode. In triggered mode, the user initiates the data transmission by sending a command through the user input interface of the mobile computing unit to instruct the mobile application start the communication session. In automatic mode, the mobile application is configured to exchange data with the remote server on periodic basis, e.g. at programmed time of the day or at programmed time intervals. In mixed mode, both manual triggered and automatic data transmission are supported. Frequency of the data transmission can be limited (e.g. not more than 1 time per X minutes, where X is a programmable parameter that defines the shortest duration between two consecutive data transmissions) to prevent repeated transmission of the same UVI data.

In one embodiment, the UV dosimetry system also has a build-in temperature sensing unit such as a temperature sensor, and the measured temperature data is also sent to the remote server, together with the measured UVI data and the time and location information of the measurement.

The remote server runs a database management software operative to analyze the data transmitted from the UV meters including UVI, time, location, and/or temperature measurement, and generates UVI maps for other users to use. The UVI maps are preferably updated periodically according to a predefined time interval.

According to this disclosure, the remote server maintains a database that aggregates the data transmitted from the UV measurement devices. The database management software controls the quality of the data collection through a plurality of filters with programmable parameter settings. Quality control of crowd sourced data is important because invalid UVI measurements may be inadvertently sent by the users. For example, a person staying indoors or under the shade may not measure the actual UVI in the local area accurately. Such misleading UVI data shall be excluded from the database.

In one exemplary embodiment, the database management software in the remote server retrieves forecasted UVI data and/or temperature data at different time and geographical locations from trusted sources or official websites, e.g., www.epa.gov, www.weather.gov, etc. User transmitted UVI measurement and/or temperature measurement data are compared with the forecast data at the corresponding time and location. Here, the corresponding time means that the difference between the time of the forecast data and the time of the UVI and/or temperature measurement is below a predefined time limit, e.g. 10 minutes, and the corresponding location means the distance between the location of the forecast data and the location of the UVI and/or temperature measurement is shorter than a predefined distance limit, e.g. 1 mile User transmitted measurement data is deemed invalid if there is substantial deviation between measured data and the corresponding forecast data, e.g. if they differ by more than a predefined tolerance value.

In another exemplary embodiment, the official forecast data is only used as a reference to reject invalid measurement data when the sample size of the measurement data at specific time period and location is limited. As more user transmitted measurement data at specific time period and location is available and included in the database, the weight of using official forecast data as a reference is reduced. Meanwhile, more weight is given to the user transmitted data, which can self-serve as the reference to reject invalid user input.

For example, when the sample size of UVI and/or temperature data measured during a specific time period and from a specific location is sufficiently large (e.g. greater than a predefined threshold), the expected normal range of UVI and/or temperature at said specific time period and location can be calculated based on the statistical distribution of the measured UVI and/or temperature data (e.g. the mean and standard deviation, or the median and inter-quartile range). Outlier measurement data falling outside the expected normal range will then be deemed invalid.

For the UVI (or temperature) data at specific time and specific location, the sample size is defined as the total number of UVI (or temperature) data measured during a time period that is close to said specific time (e.g. within a predefined time interval), and from a region that is centered around said location (e.g. within a predefined distance).

Through crowd sourcing, the UVI data is updated in the remote server database in real-time, and the UVI map can be updated periodically according to a predefined frequency. As more users contribute to the database, the reliability and accuracy of the data increases. The coverage of the UVI data on the map can be as broad as the users can go and the spatial resolution can be as fine as the GPS allows. It also allows people who do not have a UV measurement device to obtain real-time UVI information by accessing the crowd sourced UVI database through a communication network, such as the internet.

While the invention has been described with reference to exemplary embodiments, it shall be understood by those skilled in the art that various changes may be made and equivalents may be substituted without departing from the scope of the invention. In addition, many modifications may be made to adapt a particular situation or component to the teachings of the invention without departing from its scope. Therefore, it is intended that the invention not be limited to the particular embodiment disclosed, but that the invention will include all embodiments falling within the scope of the appended claims.

We claim:

1. A device comprising:
   a UV sensing unit comprising a circuitry for measuring irradiating UV intensity; and
   a mobile computing unit, wherein the mobile computing unit is a non-transitory computer readable medium having computer executable instructions stored thereon, said instructions control at least one processor to:
   receive UV intensity data measured by the UV sensing unit; and
   generate extrapolated UV intensity data repeatedly in running windows of received UV intensity data, each running window has a predefined duration.

2. The device of claim 1 is adapted to calculate exposed UV dose for a user of the device based on the extrapolated UV intensity data.

3. The device of claim 1 is adapted to calculate cutaneous vitamin D generation for a user of the device based on the extrapolated UV intensity data.

4. The device of claim 1 is adapted to calculate daily sun exposure time based on the extrapolated UV intensity data.

5. The device of claim 1, wherein generating extrapolated UV intensity data in a running window comprising:
   counting a number (G) of measured UV intensity values that are greater than or equal to a predefined UV intensity threshold in the running window;
   finding a maximum UV intensity value (UVMAX) in the running window;
   setting extrapolated UV intensity values to MIN(G, C)/C× UVMAX in the running window if G>0, wherein C is a predefined constant; and
   setting extrapolated UV intensity values to measured UV intensity values in the running window if G=0.

6. The device of claim 5, wherein the UV sensing unit has multiple UV sensors, each UV sensor measures irradiating UV intensity, and UVMAX is the maximum UV intensity value measured by all UV sensors in the running window.

7. The device of claim 1, wherein the running windows are overlapping.

8. The device of claim 1, wherein the running windows are non-overlapping.

9. A system comprising:
   a wearable unit comprising a circuitry for measuring irradiating UV intensity; and
   a mobile computing device having computer executable program stored thereon, said program controls at least one processor to:
   receive UV intensity data measured by the wearable unit; and
   generate extrapolated UV intensity data repeatedly in running windows of
   received UV intensity data, each running window has a predefined duration.

10. The system of claim 9 is adapted to calculate exposed UV dose for a user of the system based on the extrapolated UV intensity data.

11. The system of claim 9 is adapted to calculate cutaneous vitamin D generation for a user of the system based on the extrapolated UV intensity data.

12. The system of claim 9 is adapted to calculate daily sun exposure time based on the extrapolated UV intensity data.

13. The system of claim 9, wherein generating extrapolated UV intensity data in a running window comprising:
   counting a number (G) of measured UV intensity values that are greater than or equal to a predefined UV intensity threshold in the running window;
   finding a maximum UV intensity value (UVMAX) in the running window;
   setting extrapolated UV intensity values to MIN(G, C)/C× UVMAX in the running window if G>0, wherein C is a predefined constant; and
   setting extrapolated UV intensity values to measured UV intensity values in the running window if G=0.

14. The system of claim 13, wherein the wearable unit has multiple UV sensors, each UV sensor measures irradiating UV intensity, and UVMAX is the maximum UV intensity value measured by all UV sensors in the running window.

15. The system of claim 9, wherein the running windows are overlapping.

16. The system of claim 9, wherein the running windows are non-overlapping.

17. A non-transitory computer readable medium having computer executable instructions stored thereon, said instructions control at least one processor to implement a method to correct unreliable UV measurement, the method comprising:
   measuring UV intensity irradiating on a device; and
   generating extrapolated UV intensity data repeatedly in running windows of measured UV intensity data, each running window has a predefined duration.

18. The non-transitory computer readable medium of claim 17 is adapted to calculate exposed UV dose and cutaneous vitamin D generation for a user of the device based on the extrapolated UV intensity data.

19. The non-transitory computer readable medium of claim 17, wherein generating extrapolated UV intensity data in a running window comprising:
   counting a number (G) of measured UV intensity values that are greater than or equal to a predefined UV intensity threshold in the running window;
   finding a maximum UV intensity value (UVMAX) in the running window;
   setting extrapolated UV intensity values to MIN(G, C)/C× UVMAX in the running window if G>0, wherein C is a predefined constant; and
   setting extrapolated UV intensity values to measured UV intensity values in the running window if G=0.

20. The non-transitory computer readable medium of claim 19, wherein the device has multiple UV sensors, each UV sensor measures irradiating UV intensity, and UVMAX is the maximum UV intensity value measured by all UV sensors in the running window.

* * * * *